US010786234B2

(12) United States Patent
Burkhart

(10) Patent No.: US 10,786,234 B2
(45) Date of Patent: Sep. 29, 2020

(54) SUTURE ANCHOR ASSEMBLY WITH UNIVERSAL INSERTER DEVICE

(71) Applicant: Arthrex, Inc., Naples, FL (US)

(72) Inventor: Stephen S. Burkhart, Boerne, TX (US)

(73) Assignee: Arthrex, Inc., Naples, FL (US)

( * ) Notice: Subject to any disclaimer, the term of this patent is extended or adjusted under 35 U.S.C. 154(b) by 145 days.

(21) Appl. No.: 15/469,976

(22) Filed: Mar. 27, 2017

(65) Prior Publication Data
US 2018/0271514 A1    Sep. 27, 2018

(51) Int. Cl.
*A61B 17/00* (2006.01)
*A61B 17/04* (2006.01)

(52) U.S. Cl.
CPC ........ *A61B 17/0401* (2013.01); *A61B 2017/00473* (2013.01); *A61B 2017/00477* (2013.01); *A61B 2017/044* (2013.01); *A61B 2017/0409* (2013.01); *A61B 2017/0414* (2013.01); *A61B 2017/0445* (2013.01); *A61B 2017/0458* (2013.01)

(58) Field of Classification Search
CPC ........ A61B 17/0401; A61B 2017/0409; A61B 2017/0445; A61B 2017/0454; A61B 2017/0414; A61B 17/8615; A61B 17/862; A61B 17/861; A61B 17/8605; A61B 17/7258
See application file for complete search history.

(56) References Cited

U.S. PATENT DOCUMENTS

| 6,544,281 | B2 | 4/2003 | ElAttrache et al. | |
|---|---|---|---|---|
| 7,239,272 | B2 | 7/2007 | Vyas et al. | |
| 8,663,279 | B2 | 3/2014 | Burkhart et al. | |
| 2008/0004659 | A1* | 1/2008 | Burkhart | A61B 17/0401 606/232 |
| 2008/0208253 | A1* | 8/2008 | Dreyfuss | A61B 17/0401 606/232 |
| 2013/0006302 | A1* | 1/2013 | Paulk | A61B 17/0401 606/232 |
| 2014/0081375 | A1* | 3/2014 | Bardill | A61F 2/966 623/1.12 |
| 2014/0379028 | A1* | 12/2014 | Lo | A61B 17/0401 606/232 |
| 2018/0185019 | A1* | 7/2018 | Lunn | A61B 17/0401 |

* cited by examiner

*Primary Examiner* — Diane D Yabut
*Assistant Examiner* — Majid Jamialahmadi
(74) *Attorney, Agent, or Firm* — Blank Rome LLP

(57) ABSTRACT

An inserter device that has a driver, a removable inserter tip (or plurality of inserter tips) and a cannulation device slidable over the inserter tip is provided, wherein the removable inserter tip is provided as an interchangeable component of the device, one configuration of the interchangeable inserter tip being of a substantially hexagonal cross-sectional shape (suitable for accommodating a screw-in fixation device (screw), and another configuration of the interchangeable inserter tip being of a substantially circular cross-sectional shape (suitable for accommodating a push-in anchor). A suture anchor assembly has the inserter device that is used with a plug-in anchor, a screw-in anchor, or interchangeably with a plug-in or screw-in anchor, is also disclosed. A method for assembling the suture anchor assembly as well as a method of using the surgical assembly for tissue repair are also provided.

21 Claims, 4 Drawing Sheets

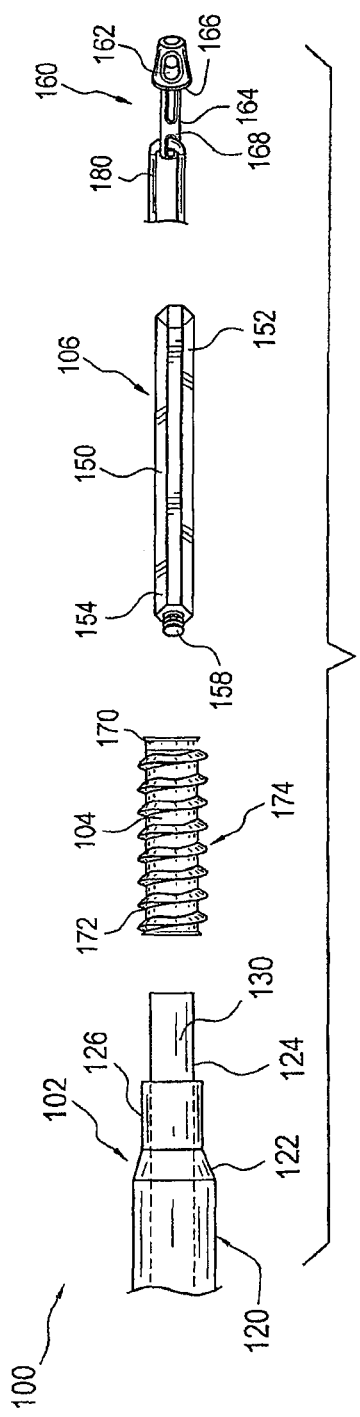

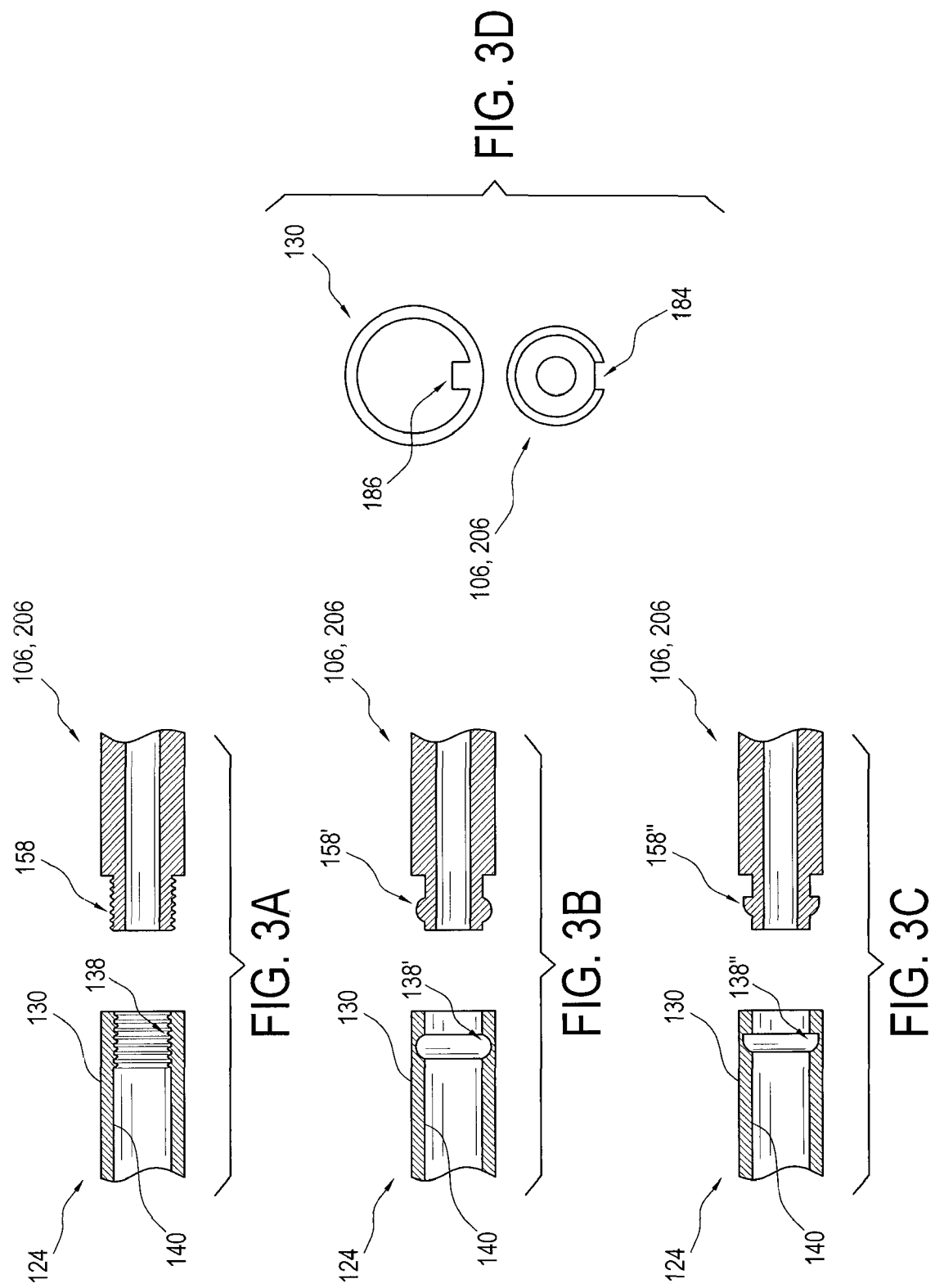

SUTURE ANCHOR ASSEMBLY WITH UNIVERSAL INSERTER DEVICE

FIELD OF THE INVENTION

The present invention relates to the field of surgical devices useful for inserting an anchor, screw or plug. In particular, the invention relates to the field of inserter devices as well as suture anchor assemblies that may include an inserter device, that may be used to insert an anchor, screw or plug of differing configurations. More specifically, the present invention relates to a universal inserter device.

BACKGROUND OF THE INVENTION

Various types of suture anchors have been developed for securing soft tissue to bone. For example, commonly assigned U.S. Pat. No. 6,544,281 to ElAttrache et al., U.S. Pat. No. 7,329,272 to Burkhart et al., and U.S. Pat. No. 8,663,279 to Burkhart et al., the subject matter of each of which is herein incorporated by reference, discloses suture anchors and anchor assemblies for use in tissue repair procedures. These inserter devices, however, are configured such that they may be used with only one type of anchor, i.e. either a ribbed, push-in anchor or a threaded rotatably advanced anchor, not both. A need exists for an improved and interchangeable inserter device that may be included with an anchor, such as a for suture anchor, that may further be incorporated as part of a suture anchor assembly suitable for insertion of a plug-type anchor or a screw-in anchor.

SUMMARY OF THE INVENTION

Accordingly, the present invention may provide in one aspect, an inserter device that is interchangeably adaptable for use with an anchor of differing configurations, is provided, For example, the inserter device may be configured to interchangeably accommodate an anchor that is either a screw-in anchor or a plug-in anchor. The anchor may be a suture anchor having a ribbed, push-in configuration (a push-in anchor) or a suture anchor having a threaded, rotatably advanced configuration (a screw-in anchor).

The inserter device may comprise a driver having an outer shaft and an inner shaft, the inner shaft being at least partially received in the outer shaft and having an opposing proximal end and distal end, the distal end of the inner shaft comprising a first engagement, a removable inserter tip having a proximal end and a distal end configured to releasably couple an anchor to the inner shaft first engagement, and a cannulation fixation device. The distal end of the removable inserter tip may further be described as an interchangeable removable inserter tip, wherein the interchangeable removable inserter tip may be releasably coupled onto the inner shaft first engagement of the driver. The removable inserter tip may be provided as a screw-on post or a snap-on post suitable for releasably coupling the tip onto the distal end of the driver.

The inserter device may include a removable inserter tip that has opposing proximal and distal ends, and the proximal end of the removable inserter tip having a second engagement configured for releasable connection to the first engagement of the distal end of the driver inner shaft. The distal end of the removable inserter tip may be configured to releasably couple an anchor, such as a plug-in anchor or a screw-in type anchor, the anchor providing for the capture of one or more sutures. A cannulated fixation device may be received on the removable inserter tip such that the cannulated fixation device is slidable over the removable inserter tip along a longitudinal axis thereof. In one embodiment, the first and second engagements are threaded engagements.

The present invention also contemplates a kit comprising an anchor assembly, such as a suture anchor assembly. In one embodiment, the anchor assembly may comprise an anchor and an inserter device that has a driver, the driver including an outer shaft and an inner shaft that is at least partially receivable in the outer shaft, and the inner shaft having opposing proximal and distal ends, where the distal end of the inner shaft has a first engagement; and one or more removable inserter tips where each of the removable inserter tips has opposing proximal and distal ends, and the proximal end of each of the removable inserter tips has a second engagement configured for releasable connection to the first engagement of the distal end of the inner shaft. The anchor assembly may also comprise at least one cannulated fixation device configured to be slidably received on at least one of the removable inserter tips; and at least one anchor configured to be releasably coupled to the distal end of any one of the removable inserter tips, and the anchor being configured to capture one or more sutures. The kit may include at least one removable and interchangeable inserter tip configured as a removable screw-on post inserter tip, or at least one removable inserter tip configured as a removable snap-on post inserter tip, or both a screw-on post inserter tip and a snap-on post inserter tip. The screw-on post and the snap-on post inserter tip shall be configured so as to be interchangeably engaged at the distal end of the inner shaft.

The present invention further provides a method of assembling a suture anchor assembly, comprising the steps of: providing an inserter device having a driver including an outer shaft and an inner shaft that is at least partially received in the outer shaft, the inner shaft having opposing proximal and distal ends; selecting a removable inserter tip, each inserter tip having an opposing proximal and distal ends; releasably engaging the proximal end of the removable inserter tip with the distal end of the inner shaft; and sliding a cannulated fixation device onto the distal end of the inner shaft and onto the proximal end of the removable inserter tip along a longitudinal axis thereof. The method also includes the step of releasably coupling an anchor implant to the distal end of the removable inserter tip, where the anchor is configured to capture one or more sutures.

It should be understood that any of the above embodiments may include a plurality of inserter tips as part of the inserter device or suture anchor assembly.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawing figures:

FIG. 1A is an exploded elevational view of a suture anchor assembly with inserter device according to an exemplary embodiment of the present invention;

FIG. 2A is an exploded elevational view of a suture anchor assembly according to an exemplary embodiment of the present invention;

FIGS. 3A-3C are each partial exploded cross-sectional view of exemplary engagement mechanisms for the suture anchor assembly according to the first and second exemplary embodiments of the present invention;

FIG. 3D is an exploded plan view of an exemplary engagement mechanism for the suture anchor assembly according to the first and second exemplary embodiments of the present invention;

DETAILED DESCRIPTION OF THE PREFERRED EMBODIMENTS

Figure 1B:
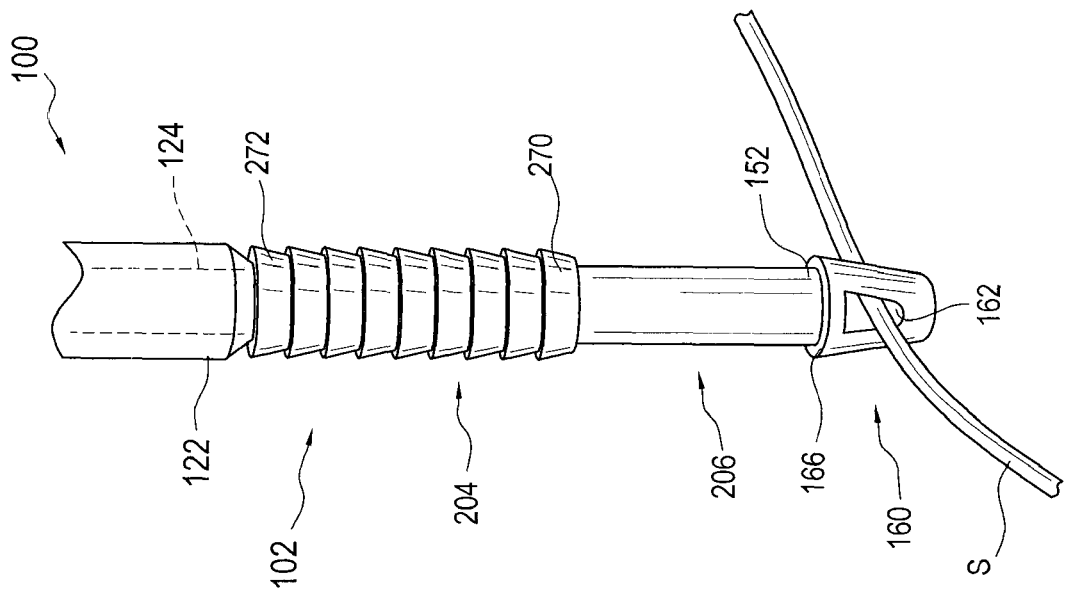
FIG. 1B a partial elevational of the suture anchor assembly illustrated in FIG. 1A, showing the suture anchor assembled and preloaded with a suture.

Referring to FIGS. 1-5, the present invention generally relates to a suture anchor assembly 100 with an inserter device 102 used for surgical tissue repair. The inserter device 102 of the present invention is designed to be universal, that is it may be used with different fixation devices. In other words, a surgeon may select a fixation device from multiple fixation devices for the suture anchor assembly 100 that is appropriate for a particular type of tissue repair using the same inserter device 102. This eliminates the need to have multiple surgical instruments each with a different inserter device required for a particular fixation device (anchor) or for a specific type of tissue repair.

Suture anchor assembly 100 generally includes the inserter device 102, a fixation device 104 (FIG. 1A), 204 (FIG. 2A), and one or more removable inserter tips, such as a first removable inserter tip 106 (FIG. 1A) and a second removable inserter tip 206 (FIG. 2A). As explained more fully below, the inserter tip 106 and inserter tip 206 are interchangeable depending on the type of fixation device (anchor) being implanted.

Figure 5:
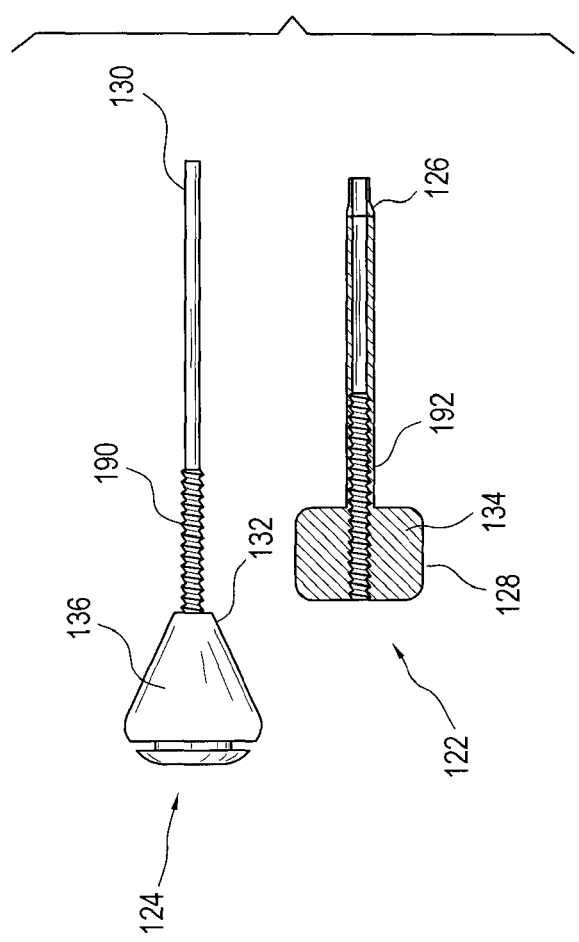
FIG. 5 is an exploded view of the inserter device illustrated in FIG. 4.

Inserter device 102 generally includes a driver 120 with an outer shaft 122 and an inner shaft 124 received in outer shaft 122. Outer shaft 122 has opposing distal and proximal ends 126 and 128. Likewise, inner shaft 124 has opposing distal and proximal ends 130 and 132 generally corresponding to the distal and proximal ends 126 and 128 of outer shaft 122. Proximal end 128 of outer shaft 122 may include a thumb pad 134 (FIG. 5) to facilitate holding of the outer shaft 122. Proximal end 132 of the inner shaft 124 may be provided with a handle 136 (FIG. 5). Distal end 130 of the inner shaft 124 includes a first engagement 138 (FIG. 3A), 138' (FIG. 3B), and 138" (FIG. 3C) for coupling to one of the removable inserter tips 106, 206.

Figure 2B:
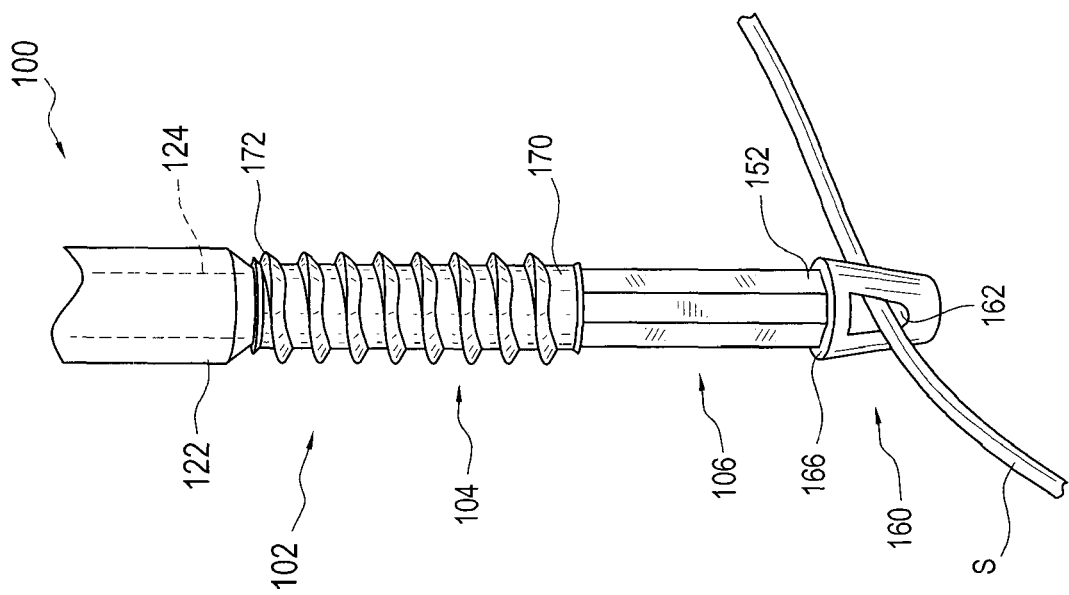
FIG. 2B a partial elevational of the suture anchor assembly illustrated in FIG. 2A, showing the suture anchor assembled and preloaded with a suture.
Figure 4:
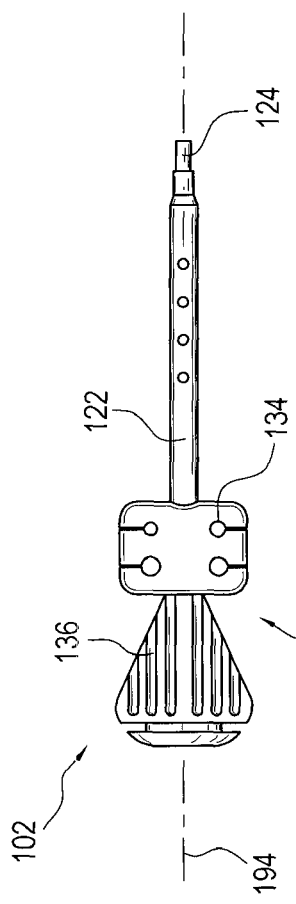
FIG. 4 is an elevational view of the inserter device of the present invention that may be used with the suture anchor assembly of either the first or second embodiment.

Each removable inserter tip 106, 206 has a cannulated elongated body 150, 250 with a distal end 152 and a proximal end 154. The elongated body 150 of removable inserter tip 106 preferably has an outer shape that is substantially hexagonal, as seen in FIGS. 1A and 1B. That is, in cross-section, the outer surface of the elongated body 150 of the removable inserter tip 106 has a substantially hexagonal shape. This hexagonal shape configuration provides for the insertion of a screw-in anchor. The elongated body 250 of the removable inserter tip 206 has a substantially cylindrical shape, as seen in FIGS. 2A and 2B. That is, in cross-section, the outer surface of elongated body 250 has a substantially circular shape. This circular shape configuration provides for the insertion of a plug-type anchor.

Proximal end 154 of the elongated body 150, 250 includes a second engagement 158 (FIG. 3A), 158' (FIG. 3B), or 158" (FIG. 3C) for releasable connection to the distal end 130 of the inner shaft 124. As seen in FIG. 3A, the first and second engagements 138 and 158, may be a threaded engagement. For example, first engagement 138 may be internal threads disposed on the inner surface 140 at the inner shaft's distal end 132, and second engagement 158 may be a post with outer threads for coupling with the inner threads of the first engagement 138. As seen in FIG. 3B, the first engagement 138' may be a groove on the inner surface 140 at the inner shaft's distal end 132, and second engagement 158' may be a post with an outer rib substantially surrounding the post that snap fits into the groove of first engagement 138'. As seen in FIG. 3C, the first engagement 138" may be an angular channel on the inner surface 140 at the inner shaft's distal end 132, and the second engagement 158" may be a post with an outer angular rib substantially surrounding the post that snap fits into the annular channel of first engagement 138". The annular channel and angular rib of FIG. 3C preferably have corresponding right angles that contact one another to provide additional stability when snapping in removable tip 106, 206. The first and second engagements may optionally include an alignment feature, as seen in FIG. 3D. For example, the alignment feature may be a notch 184 disposed in the outer angular rib 138" and a corresponding tooth 186 disposed on the inner shaft's distal end 130. This also provides a breach in the snap fit to allow disengagement when the tooth and the notch are aligned. It will be appreciate that other types of engagements may be used, such as a snapping engagement and the like, to couple each removable inserter tip 106, 206 to the inner shaft's distal end 130. The distal end 152 of each removable inserter tip 106, 206 is configured to releasably couple to an anchor implant 160.

Cannulated fixation device 104 (FIG. 1A) is designed to receive the proximal end 154 of the removable inserter tip 106 at its distal end 170 and designed to receive the distal end 130 of inner shaft 124 at its proximal end 172, as best seen in FIG. 1B. This allows the cannulated fixation device 104 to slide over the removable inserter tip 106. Fixation device 104 is preferably an interference screw, such as disclosed in U.S. Pat. No. 8,663,279 to Burkhart et al. The screw anchor 104 has outer screw threads 174 for engaging the inner surface of, for example, a bone in which a hole has been drilled. The inner cannulation of the screw anchor preferably has a substantially hexagonal shape corresponding to the shape of the removable inserter tip 106.

Cannulated fixation device 204 (FIG. 2A) is designed to receive the proximal end 154 of the removable inserter tip 206 at its distal end 270 and also designed to receive the distal end 130 of inner shaft 124 at its proximal end 272, as best seen in FIG. 2B. This allows the cannulated fixation device 204 to slide over the removable inserter tip 206. Fixation device 204 is preferably a push-in anchor, such as disclosed in U.S. Pat. No. 7,329,272 to Burkhart et al. The push-in anchor 204 has outer barbs 274 for engaging the inner surface of the hole bored in bone and its inner cannulation has a substantially cylindrical shape to correspond to the shape of the removable inserter tip 206.

The anchor implant 160 is preferably a swivel implant, such as disclosed in U.S. Pat. No. 8,663,279 to Burkhart et al. The implant 160 may include an eyelet 162 for receiving one or more sutures S (FIGS. 2A and 2B). The one or more sutures S may be any type of flexible strand or tape used in tissue repair. Although eyelet 162 is preferred, it will be appreciated that the implant 160 may include any mechanism for receiving or capturing one or more sutures, such as a forked end and the like. A shaft extension 164 extends from eyelet 162 and is receivable in the distal end 152 of the removable inserter tip 106, 206. A shoulder 166 is defined between the eyelet 162 and the shaft extension 164 for abutting against the distal end 152 when the implant 160 is received in the cannulation of the distal end 152.

One or more traction sutures 180, such as those disclosed in U.S. Pat. No. 8,663,279 to Burkhart et al., may be used with the implant 160 to prevent inadvertent separation of the implant 160 from the removable inserter tip 106, 206 during handling and insertion. The traction sutures 180 are coupled to a proximal end 168 of the implant 160, such as by extending the traction sutures 180 through an opening in the proximal end 168. The traction sutures 180 may then be threaded through the cannulation of the removable inserter tip 106, 206, the fixation device 104, 204, and the inner shaft 124 of the inserter device.

As seen in FIG. 5, the inner shaft 124 preferably has outer threads 190 near its proximal end 132 and the outer shaft 122 may have corresponding inner threads 192 near its proximal end 128. The outer threads 190 are oriented in a direction opposite to the orientation of the inner threads 192, thereby defining a reverse thread region of the inserter device 102. The reverse thread engagement between the outer and inner shafts 122 and 124 allows advancement of the inner shaft 124 along the longitudinal axis 194 (FIG. 4) of the insert device.

The suture anchor assembly 100 with the inserter device 102 of the present invention may be assembled by selecting a removable inserter tip 106 or 206 and releasably engaging the proximal end 154 of the selected removable inserter tip 106 or 206 with the distal end 130 of the inner shaft 124 by coupling the first and second engagements 138 and 158 (FIG. 3). The fixation device 104 or 204 which corresponds to the selected removable inserter tip 106 or 206 is also slid onto the distal end 130 of the inner shaft 124 and onto the proximal end 154 of the selected removable inserter tip 106 or 206 along the longitudinal axis 194 of the inserter device such that both are received in the cannulation of the fixation device 104 or 204. The implant 160 may be releasably coupled to the distal end 152 of the selected removable inserter tip 106 or 206, such as by using the traction sutures 160.

With the anchor implant 160 seated on the tip of the inserter device, the implant 160 may be loaded with one or more sutures S and then placed in a pre-formed bone hole. If inserter tip 106 is used, the inner shaft 124 of the inserter device 102 is then be rotated, using handle 136, while holding the outer shaft 122 stationary using thumb pad 134, to advance the inner shaft 124 and the fixation device 104 down the selected removable inserter tip 106 along the longitudinal axis 194 to secure the implant 160 and sutures S in the bone hole. Alternatively, if the inserter tip 206 is used, the inner shaft 124 and the fixation device 204 may be advanced down the selected removable inserter tip 206 into the bone hole by tapping or hammering the proximal end 132 of the inner shaft 124. Once the fixation device 104 or 204 and the sutures S are installed in the bone hole, the inserter deice 102 may then be removed leaving the sutures S to be used for the tissue repair.

While particular embodiments have been chosen to illustrate the invention, it will be understood by those skilled in the art that various changes and modifications can be made therein without departing from the scope of the invention as defined in the appended claims.

What is claimed is:

1. An inserter device, comprising:
a driver comprising an outer shaft and an inner shaft, the inner shaft being at least partially received in the outer shaft and having opposing proximal and distal ends, wherein the distal end of the inner shaft comprises a first engagement;
a removable inserter tip having opposing proximal and distal ends and a longitudinal axis extending between the proximal and distal ends, the proximal end of the removable inserter tip having a second engagement configured for releasable connection to the first engagement of the distal end of the inner shaft, and the distal end of the removable inserter tip defining an opening along the longitudinal axis configured to receive and releasably couple with an anchor; and
a cannulated fixation device configured to directly contact and slide axially over at least the proximal end of the removable inserter tip.

2. The inserter device according to claim 1, wherein the removable inserter tip has a substantially hexagonal cross-sectional shape.

3. The inserter device according to claim 2, wherein the cannulated fixation device is a screw having a cannulation that is substantially hexagonally shaped.

4. The inserter device according to claim 1, wherein the removable inserter tip has a substantially circular cross-sectional shape.

5. The inserter device according to claim 1, wherein the cannulated fixation device is a push-in anchor having a cannulation that is substantially circular shaped in cross-section.

6. The inserter device according to claim 1, wherein the first engagement comprises internal threads; and the second engagement comprises a post with outer threads that is receivable in the distal end of the inner shaft to couple with the first engagement.

7. The inserter device according to claim 1, further comprising the anchor, wherein the anchor comprises an eyelet.

8. An inserter kit for a suture anchor assembly, comprising:
an inserter device having a driver including an outer shaft and an inner shaft that is at least partially receivable in the outer shaft, the inner shaft having opposing proximal and distal ends, the distal end of the inner shaft having a first engagement;
a plurality of removable inserter tips, each of the plurality of removable inserter tips having an outer surface and opposing proximal and distal ends, the proximal end of each of the plurality of removable inserter tips having a second engagement configured for releasable connection to the first engagement of the distal end of the inner shaft, wherein the outer surface of a first one of the removable inserter tips has a first cross-sectional profile, and the outer surface of a second one of the removable inserter tips has a second cross-sectional profile that is different from the first cross-sectional profile;
a first cannulated fixation device configured to be slidably received on the first removable inserter tip; and
a second cannulated fixation device configured to be slidably received on the second removable inserter tip.

9. The kit according to claim 8, further comprising
at least one anchor configured to be releasably coupled to the distal end of at least one of the removable inserter tips, the at least one anchor being configured to capture one or more sutures.

10. The kit according to claim 8, wherein
at least one of the removable inserter tips has a substantially hexagonal cross-sectional shape.

11. The kit according to claim 10, wherein
each of the at least one of the removable inserter tips that has a substantially hexagonal cross-sectional shape comprises a detachable screw-on tip attachment suitable for engagement with a screw-in anchor.

12. The kit according to claim 8, wherein
at least one of the removable inserter tips has a substantially circular cross-sectional shape.

13. The kit according to claim 12, wherein
each of the at least one of the removable inserter tips that has a substantially circular cross-sectional shape comprises a detachable snap-on tip attachment suitable for engagement with a plug-in anchor.

14. The kit according to claim 8, wherein
the first removable inserter tip has a substantially hexagonal cross-sectional shape and the second removable inserter tip has a substantially circular cross-sectional shape.

15. The kit according to claim 8, wherein
the first cannulated fixation device is a screw.

16. The kit according to claim 8, wherein
the second cannulated fixation device is a push-in anchor.

17. The kit according to claim 8, wherein
the first engagement comprises internal threads; and the second engagement comprises a post with outer threads that is receivable in the distal end of the inner shaft to couple with the first engagement.

18. The kit according to claim 8, further comprising
an anchor that comprises an eyelet.

19. An inserter device, comprising:
a driver comprising an outer shaft and an inner shaft, the inner shaft being at least partially received in the outer shaft and having opposing proximal and distal ends, wherein the distal end of the inner shaft comprises a first engagement;
a removable inserter tip having opposing proximal and distal ends, the proximal end of the removable inserter tip having a second engagement configured for releasable connection to the first engagement of the distal end of the inner shaft;
a cannulated fixation device that is slidable over the removable inserter tip along a longitudinal axis thereof; and
an anchor separable from and having a portion receivable in the distal end of the removable inserter tip.

20. The inserter device according to claim 19, wherein
the cannulated fixation device is configured to directly contact and slide over at least the proximal end of the removable inserter tip.

21. The inserter device according to claim 20, wherein
the first engagement comprises internal threads and the second engagement comprises outer threads that are receivable in the distal end of the inner shaft to couple with the internal threads thereof.

* * * * *